(12) United States Patent
Rosen et al.

(10) Patent No.: US 6,949,510 B2
(45) Date of Patent: Sep. 27, 2005

(54) USES OF DITERPENOID TRIEPOXIDES AS AN ANTI-PROLIFERATIVE AGENT

(75) Inventors: Glenn D. Rosen, Stanford, CA (US); Edwin S. Lennox, Stanford, CA (US); John H. Musser, San Carlos, CA (US)

(73) Assignees: Pharmagenesis, Palo Alto, CA (US); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/340,101

(22) Filed: Jan. 10, 2003

(65) Prior Publication Data

US 2003/0139439 A1 Jul. 24, 2003

Related U.S. Application Data

(62) Division of application No. 09/884,898, filed on Jun. 19, 2001, now Pat. No. 6,537,984, which is a division of application No. 09/385,917, filed on Aug. 30, 1999, now Pat. No. 6,294,546.

(51) Int. Cl.[7] .................. A61K 38/00; A61K 31/44; A61K 31/34
(52) U.S. Cl. ................ 514/11; 514/291; 514/468
(58) Field of Search ................ 514/11, 291, 468

(56) References Cited

U.S. PATENT DOCUMENTS

| | | | |
|---|---|---|---|
| 5,294,443 A | | 3/1994 | Lipsky et al. |
| 5,496,846 A | | 3/1996 | Wilson et al. |
| 5,759,550 A | * | 6/1998 | Wiedmann et al. ......... 514/468 |
| 5,843,452 A | * | 12/1998 | Wiedmann et al. ......... 424/759 |
| 5,919,816 A | | 7/1999 | Hausheer et al. |

FOREIGN PATENT DOCUMENTS

| | | | |
|---|---|---|---|
| WO | WO 95/15174 | | 6/1995 |
| WO | WO 97/31921 | * | 9/1997 ............. 514/468 |
| WO | WO 00/48619 | | 8/2000 |

OTHER PUBLICATIONS

Lee et al., PG490 (Triptolide) Cooperates With Tumor Necrosis Factor–α to Induce Apoptosis in Tumor Cells, The Journal of Biol. Chem., 1999, 274(19): 13451–13455.

Gu et al. (1995), "Isolation, Purification, and Characterization of Immunosuppressive Compounds from Tripterygium: Triptolide and Tripdiolide," *Int. J. Immunopharmac.*, vol. 17(5):351–356.

Lee et al. (1999), "PG490 (Triptolide) Cooperates with Tumor Necrosis Factor–α to Induce Apoptosis in Tumor Cells," *Journal of Biochemistry*, vol. 274(19):18451–18455.

Qiu et al. (1999), "Immunosuppressant PG490 (Triptolide) Inhibits T–cell Interleukin–2 Expression at the Level of Purine–box/Nuclear Factor of Activated T–cells and NF–κB Transcriptional Activation," *Journal of Biological Chemistry*, vol. 274(19):13443–13450.

Shamon et al. (1997), "Evaluation of the Mutagenic, Cytotoxic, and Antitumor Potential of Triptolide, a Highly Oxygenated Diterpene Isolated from *Tripterygium Wilfordii*," *Cancer Letters*, vol. 112:113–117.

Tengchaisri et al. (1998), "Antitumor Activity of Triptolide Against Cholangiocarcinoma Growth in Vitro and in Hamsters," *Cancer Letters*, vol. 133:169–175.

Yang et al. (1998), "Triptolide Induces Apoptotic Death of T lymphocyte," *Immunopharmacology*, vol. 40:139–149.

Lievano et al., Antitumor Effect of CPT–11, A New Derivative of Camptothecin, Against Human Prostate Cancer (PC–3) in Vitro and Prostate Rat Tumor (AT–3) in Vivo, Methods Find Exp Clin Pharmacol., 1996, 18(10): 659–62.

Wei et al., Inhibitory Effect of Triptolide on Colony Formation of Breast and Stomach Cancer Cell Lines, Cell Growth Factor Division, 1991, 12(5): 406–10.

* cited by examiner

*Primary Examiner*—Paul A. Zucker
(74) *Attorney, Agent, or Firm*—Pamela J. Sherwood; Bozicevic, Field & Francis LLP

(57) ABSTRACT

Combinations of diterpenoid triepoxides and anti-proliferative agents are used in a combination therapy to treat hyperproliferative disorders. Anti-proliferative agents of interest include agents active in killing tumor cells, as well as immunosuppressants, and a variety of other agents that reduce cellular proliferation in targeted tissues. Synergistic combinations provide for comparable or improved therapeutic effects, while lowering adverse side effects.

13 Claims, 8 Drawing Sheets

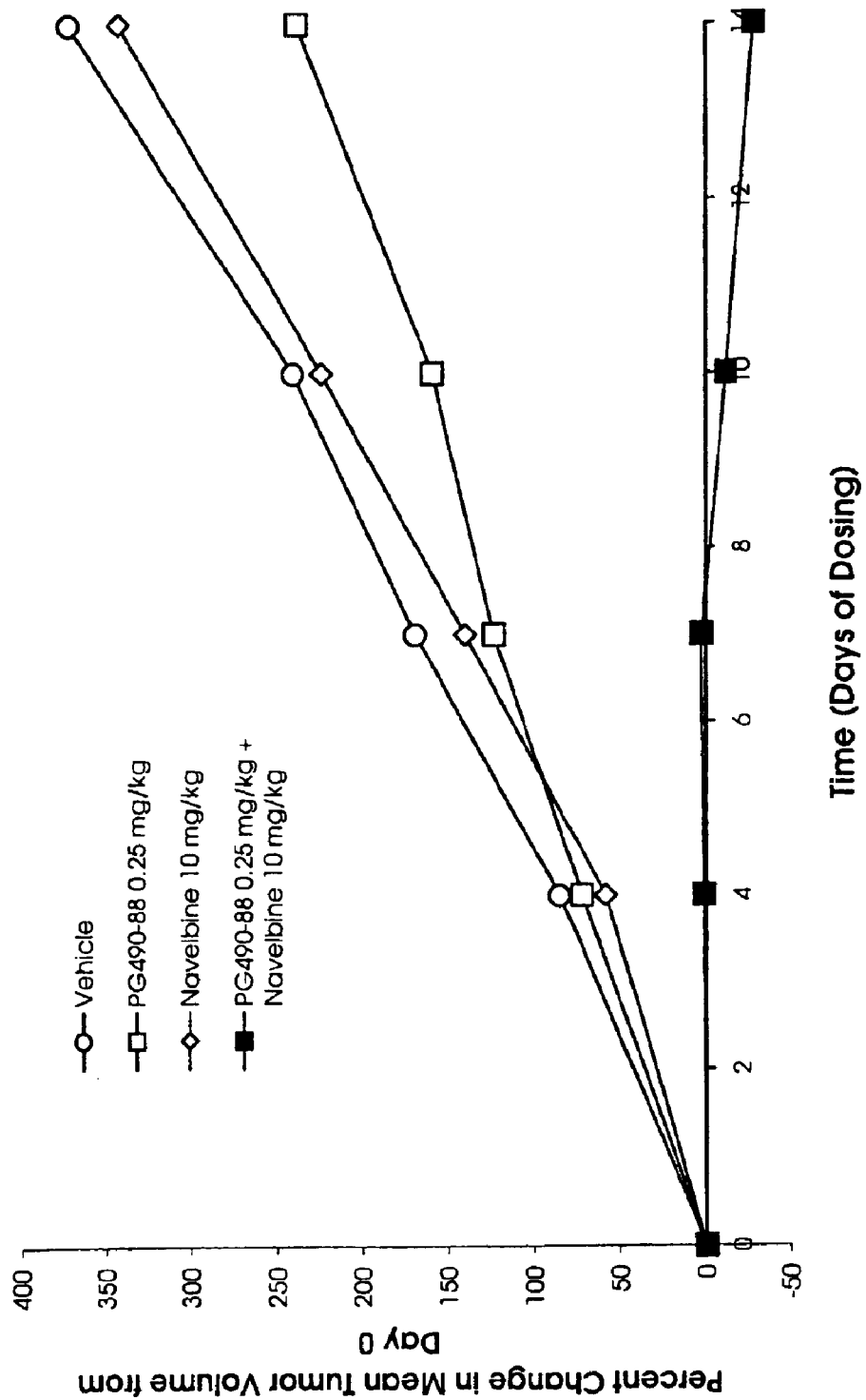

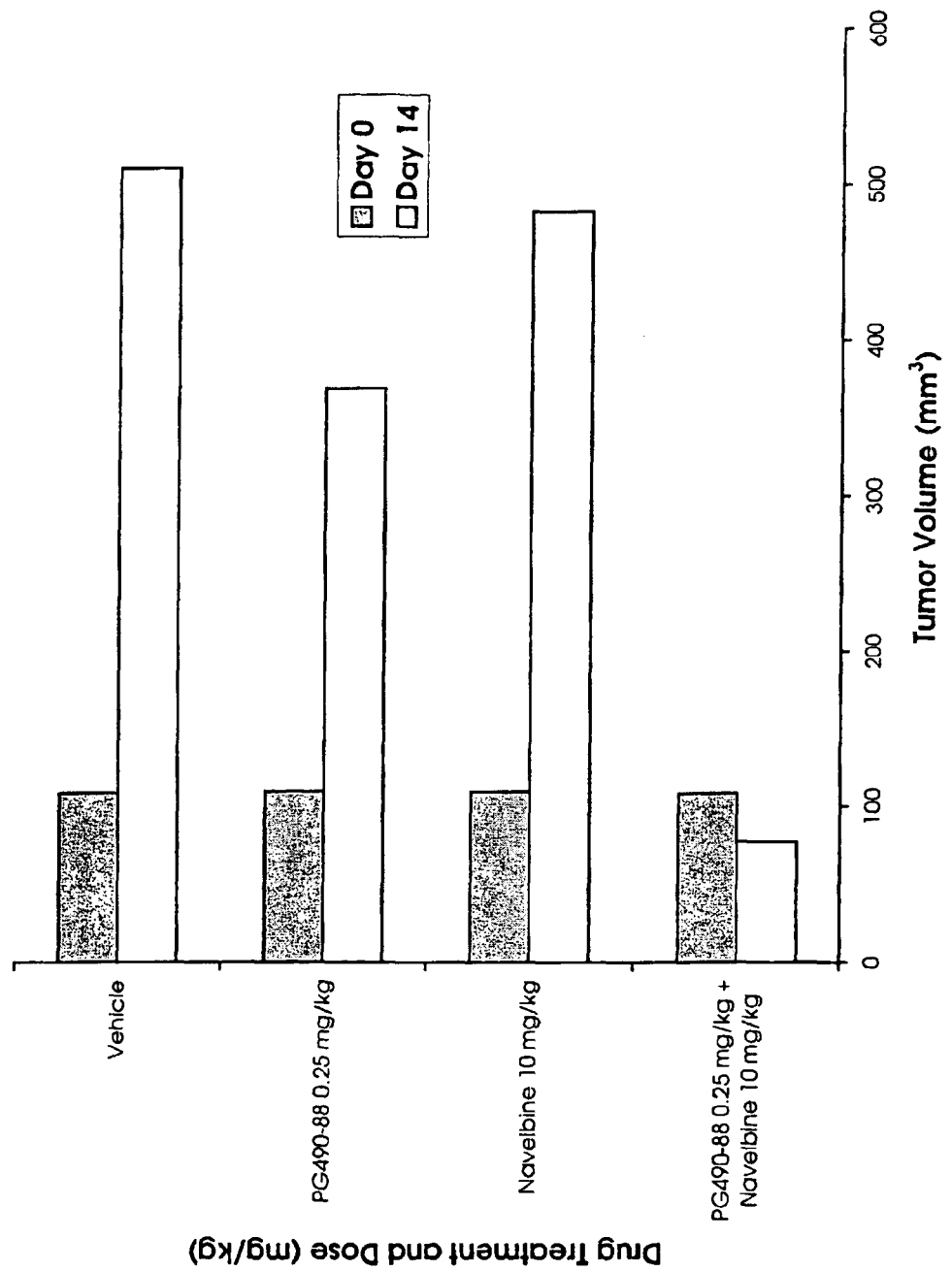

SEQUENCE LISTING

<160> NUMBER OF SEQ ID NOS: 8

<210> SEQ ID NO 1
<211> LENGTH: 20
<212> TYPE: DNA
<213> ORGANISM: H. sapiens

<400> SEQUENCE: 1
agtcagatcc tagcgtcgag                                                    20

<210> SEQ ID NO 2
<211> LENGTH: 20
<212> TYPE: DNA
<213> ORGANISM: H. sapiens

<400> SEQUENCE: 2
tcttctttgg ctggggagag                                                    20

<210> SEQ ID NO 3
<211> LENGTH: 22
<212> TYPE: DNA
<213> ORGANISM: H. sapiens

<400> SEQUENCE: 3
gtcaatcagc aggaatcatc gg                                                 22

<210> SEQ ID NO 4
<211> LENGTH: 23
<212> TYPE: DNA
<213> ORGANISM: H. sapiens

<400> SEQUENCE: 4
caatcaggaa catcaaagcc ctc                                                23

<210> SEQ ID NO 5
<211> LENGTH: 20
<212> TYPE: DNA
<213> ORGANISM: H. sapiens

<400> SEQUENCE: 5
agtggggcat catcaaaaac                                                    20

<210> SEQ ID NO 6
<211> LENGTH: 23
<212> TYPE: DNA
<213> ORGANISM: H. sapiens

<400> SEQUENCE: 6
gactccttgt tccgctgcta atc                                                23

<210> SEQ ID NO 7
<211> LENGTH: 18
<212> TYPE: DNA
<213> ORGANISM: H. sapiens

<400> SEQUENCE: 7
cccatcacca tcttccag                                                      18

<210> SEQ ID NO 8
<211> LENGTH: 18
<212> TYPE: DNA
<213> ORGANISM: H. sapiens

```
<400> SEQUENCE: 8
atgaccttgc ccacagcc                                                          18
```

USES OF DITERPENOID TRIEPOXIDES AS AN ANTI-PROLIFERATIVE AGENT

BACKGROUND

Progress in the treatment of solid tumors has been slow and sporadic despite the development of new chemotherapeutic agents. There are many roadblocks to successful chemotherapy, including drug resistance, resistance to apoptosis, and the inactivation of tumor suppressor genes. Some human cancers are drug resistant before treatment begins, while in others drug resistance develops over successive rounds of chemotherapy.

One type of drug resistance, called multidrug resistance, is characterized by cross resistance to functionally and structurally unrelated drugs. Typical drugs that are affected by the multidrug resistance are doxorubicin, vincristine, vinblastine, colchicine, actinomycin D, and others. At least some multidrug resistance is a complex phenotype that is linked to a high expression of a cell membrane drug efflux transporter called Mdr1 protein, also known as P-glycoprotein. This membrane "pump" has broad specificity and acts to remove from the cell a wide variety of chemically unrelated toxins.

Another factor in cancer therapy is the susceptibility of targeted cells to apoptosis. Many cytotoxic drugs that kill cells by crippling cellular metabolism at high concentration can trigger apoptosis in susceptible cells at much lower concentration. Increased susceptibility to apoptosis can be acquired by tumor cells as a byproduct of the genetic, changes responsible for malignant transformation, but most tumors tend to acquire other genetic lesions which abrogate this increased sensitivity. Either at presentation or after therapeutic attempts, the tumor cells can become less sensitive to apoptosis than vital normal dividing cells. Such tumors are generally not curable by conventional chemotherapeutic approaches. Although decreased drug uptake, altered intracellular drug localization, accelerated detoxification and alteration of drug target are important factors, pleiotropic resistance due to defective apoptotic response is also a significant category of drug resistance in cancer.

An important tumor suppressor gene is the gene encoding the cellular protein, p53, which is a 53 kD nuclear phosphoprotein that controls cell proliferation. Mutations to the p53 gene and allele loss on chromosome 17p, where this gene is located, are among the most frequent alterations identified in human malignancies. The p53 protein is highly conserved through evolution and is expressed in most normal tissues. Wild-type p53 has been shown to be involved in control of the cell cycle, transcriptional regulation, DNA replication, and induction of apoptosis.

Various mutant p53 alleles are known in which a single base substitution results in the synthesis of proteins that have quite different growth regulatory properties and, ultimately, lead to malignancies. In fact, the p53 gene has been found to be the most frequently mutated gene in common human cancers, and is particularly associated with those cancers linked to cigarette smoke. The overexpression of p53 in breast tumors has also been documented.

An area to search for new therapeutic interventions is that of traditional Chinese medicines. One of these traditional medicines is from *Tripteryguim wilfordii* Hook F, a shrub-like vine from the Celastraceae family. A variety of preparations derived from this plant have been used in South China for many years to treat different forms of arthritis and other autoimmune diseases. In 1978, an extract of *Tripterygium wilfordii* Hook F was produced by chloroform methanol extraction of the woody portion of the roots and designated T2. Reports in the Chinese literature describe T2 treatment of more than 750 patients with a variety of autoimmune diseases.

The Chinese experience has suggested that a daily dosage of about 1 mg/kg of T2 is safe and effective as an immunosuppressant. Acute and chronic toxicity studies have been carried out in China using a variety of animal models. The $LD_{50}$ in mice was reported to be around 150 mg/kg. The toxicity studies suggest that T2 exhibits a reasonable safety index and should be able to be administered to patients safely.

The development of chemotherapeutic agents and combinations of agents that avoid problems of drug resistance and resistance to apoptosis are of great interest for the treatment of cancer.

Relevant Literature

The isolation, purification, and characterization of immunosuppressive compounds from tripterygium: triptolide and tripdiolide is reported by Gu et al. (1995) *Int J Immunopharmacol* 17(5):351–6. Yang et al. (1998) *Immunopharmacology* 40(2):139–49 provide evidence that suggests the immunosuppressive agent triptolide inhibits antigen or mitogen-induced T cell proliferation, and induces apoptotic death of T cell hybridomas and peripheral T cells. Shamon et al. (1997) *Cancer Lett* 112(1):113–7 evaluate the antitumor potential of triptolide. Tengchaisri et al. (1998). *Cancer Lett*. 133(2):169–75 evaluate the antitumor activity of triptolide against cholangiocarcinoma growth in vitro and in hamsters.

Lee et al. (1999) *J Biol Chem* 274(19):13451–5 describe the interaction of PG490 (triptolide) with tumor necrosis factor-alpha to induce apoptosis in tumor cells. Triptolide was found to inhibit T-cell interleukin-2 expression at the level of purine-box/nuclear factor of activated T-cells and NF-kappa B transcriptional activation by Qiu et al. (1999) *J Biol Chem*. 274(19):13443–50.

SUMMARY OF THE INVENTION

Compositions and methods are provided for the use of diterpenoid triepoxides in combination with anti-proliferative agents, as a combination therapy to treat hyper-proliferative disorders. The methods and compositions are particularly useful in the treatment of multi-drug resistant tumor cells. Anti-proliferative agents of interest include agents active in killing tumor cells, as well as immunosuppressants, and a variety of other agents that reduce cellular proliferation in targeted tissues. The targeted cells are contacted with an anti-proliferative agent and diterpenoid triepoxides, e.g. triptolide, tripdiolide, etc., or prodrugs that convert to such compounds under physiological conditions, either locally or systemically. Synergistic combinations provide for comparable or improved therapeutic effects, while lowering adverse side effects.

In one embodiment of the invention, a macrocyclic immunosuppressant, e.g. FK-506 (tacrolimus, prograf); cyclosporine, rapamycin, etc.; is used in combination with triptolide or an ester thereof as an immunosuppressant, particularly with allogeneic organ transplants, as well as in the treatment of other immune disorders.

BRIEF DESCRIPTION OF THE DRAWINGS

FIG. 7. Combination treatment of nude mice bearing established HT-29 human colon cancer cell line tumors with PG490-88 and Navelbine.

FIG. 8. Combination treatment of nude mice bearing established HT-29 human colon cancer cell line tumors with PG490-88 and Navelbine.

DETAILED DESCRIPTION OF THE EMBODIMENTS

Figure 1:
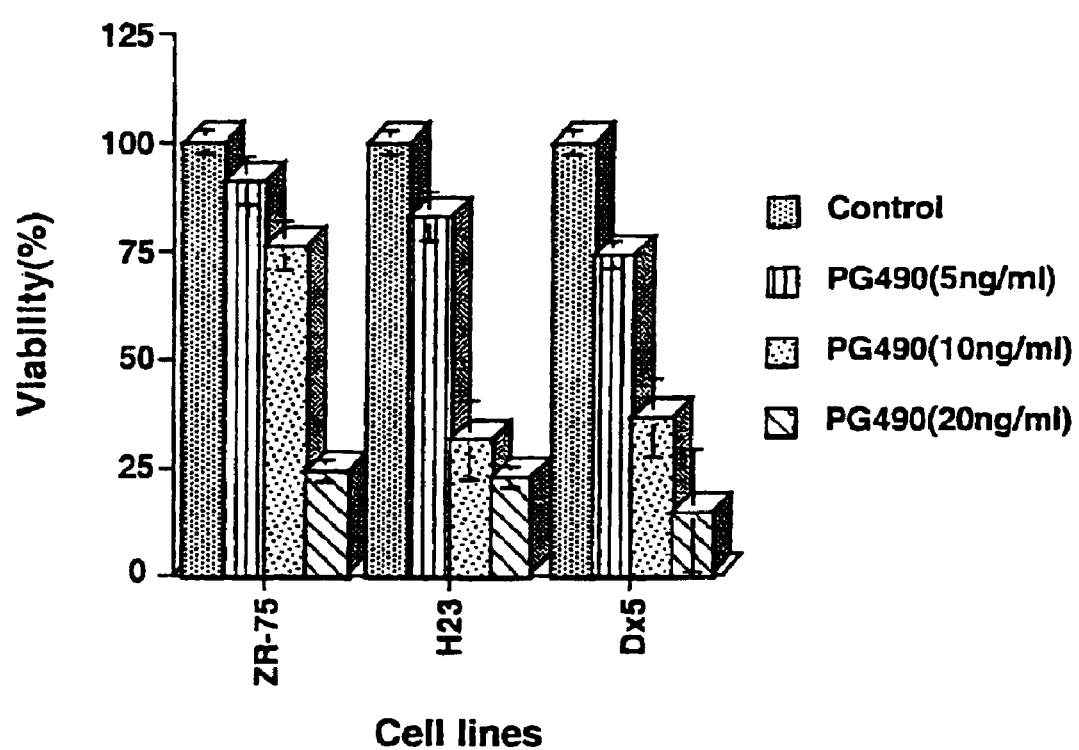
FIG. 1 is a graph depicting the cytotoxicity of PG490 in tumor cells.

Diterpenoid triepoxides are formulated in combination with anti-proliferative agents, as a combination therapy to treat hyperproliferative disorders. Although the diterpenoid triepoxides, and the anti-proliferative agents, are active when administered alone, the concentrations required for a therapeutic dose may create unacceptable side effects. The combination therapy may provide for a therapeutic effect with less toxicity.

Anti-proliferative agents of interest include agents active in killing tumor cells, as well as immunosuppressants, and a variety of other agents that reduce cellular proliferation in targeted tissues. The targeted cells are contacted with an anti-proliferative agent and diterpenoid triepoxides, e.g. triptolide, tripdiolide, etc., or prodrugs that convert to such compounds under physiological conditions, either locally or systemically. Synergistic combinations provide for comparable or improved therapeutic effects, while lowering adverse side effects. The subject methods provide a means for therapeutic treatment and investigation of hyperproliferative disorders, through the induction of a novel cell-killing pathway. Animal models, particularly small mammals, e.g. murine, lagomorpha, etc. are of interest for experimental investigations.

The subject methods are used for prophylactic or therapeutic purposes. The term "treatment" as used herein refers to reducing or alleviating symptoms in a subject, preventing symptoms from worsening or progressing, inhibition or elimination of the causative agent, or prevention of the disorder in a subject who is free therefrom. For example, treatment of a cancer patient may be reduction of tumor size, elimination of malignant cells, prevention of metastasis, or the prevention of relapse in a patient who has been cured. Treatment with an immunosuppressive agent may reduce graft rejection, symptoms of autoimmune disease, and the like. The treatment of ongoing disease, to stabilize or improve the clinical symptoms of the patient, is of particular interest. Such treatment is desirably performed prior to complete loss of function in the affected tissues.

Definitions

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention, which will be limited only by the appended claims.

Hyperproliferative disorders: refers to excess cell proliferation, relative to that occurring with the same type of cell in the general population and/or the same type of cell obtained from a patient at an earlier time. The term denotes malignant as well as non-malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the patient's life. Hyperproliferative cell disorders can occur in different types of animals and-in humans, and produce different physical manifestations depending upon the affected cells.

Hyperproliferative cell disorders include cancers; blood vessel proliferative disorders such as restenosis, atherosclerosis, in-stent stenosis, vascular graft restenosis, etc.; fibrotic disorders; psoriasis; inflammatory disorders, e.g. arthritis, etc.; glomerular nephritis; endometriosis; macular degenerative disorders; benign growth disorders such as prostate enlargement and lipomas; undesirable immune responses, e.g. rejection of grafts, and autoimmune disorders. Cancers are of particular interest, including leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, and the like.

Multidrug resistant cells: Cells of particular interest for the subject anti-proliferative therapy are multi-drug resistant. Multi-drug resistance is frequently caused by an integral glycoprotein in the plasma membrane of the targeted cell, P-glycoprotein (pleiotropic-glycoprotein, Pgp, MDR1), or a related homolog (MRP). When expressed by tumor cells, MDR1 expels cytotoxic chemotherapeutic agents, and thus allows the tumor cell to survive anticancer treatments even at high drug doses. For example, treatment with vinca alkaloids can be compromised by the development of multidrug resistance.

Various methods may be used to determine whether a particular tumor cell sample is multi-drug resistant. Multi-drug resistance can be diagnosed in tumors by molecular biology techniques (gene expression at the mRNA level), by immunological techniques (quantification of P-glycoprotein itself) or by functional approaches (measuring dye exclusion). The sequence of P-glycoprotein may be obtained as Genbank accession number NM_000927 (Chen et al. (1986) Cell 47:381–389.

In MDR1-expressing cells a decreased uptake of cytotoxic drugs can be visualized by measuring the cellular accumulation or uptake of fluorescent compounds, e.g., anthracyclines (Herweijer et al. (1989) *Cytometry* 10:463–468), verapamil-derivatives (Lelong et al. (1991) *Mol. Pharmacol.* 40:490–494), rhodamine 123 (Neyfakh (1988) Exp. Cell Res. 174:168–174); and Fluo-3 (Wall et al. (1993) *Eur. J. Cancer* 29:1024–1027). Alternatively, the sample of cells may be exposed to a calcein compound; measuring the amount of calcein compound accumulating in the specimen cells relative to control cells. Reduced calcein accumulation in specimen cells relative to control cells indicates the presence of multi-drug resistance in the biological specimen.

diterpenoid triepoxide sensitizing agent: compounds of interest for use in the combination therapy include compounds having the structure:

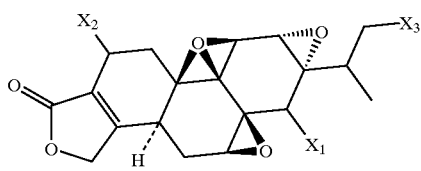

wherein $X_1$ is OH, =O; or $OR^1$;

$X_2$ and $X_3$ are independently OH, $OR^1$ or H;

$R^1$ is —C(O)—Y—Z, wherein Y is a branched or unbranched $C_1$ to $C_6$ alkyl or alkenyl group; and Z is $COOR^2$, $NR^3R^{3'}$, or $+NR^4R^{4'}R^{4''}$, where $R^2$ is a cation; $R^3$ and $R^{3'}$ are independently H or branched or unbranched $C_1$ to $C_6$ alkyl, hydroxyalkyl, or alkoxyalkyl, or $R^3$ and $R^{3'}$ taken together form a 5- to 7-member heterocyclic ring whose ring atoms are selected from the group consisting of carbon, nitrogen, oxygen and sulfur, wherein the ring atoms include 2 to 6 carbon atoms, or more nitrogen atoms, and optionally one or more oxygen or sulfur atoms, and wherein the ring is unsubstituted or is substituted with one or more groups selected from $R^5$, $OR^5$, $NR^5R^6$, $SR^5$, $NO_2$, CN, $C(O)R^5$, $C(O)NR^5R^6$, and halogen (fluoro, chloro, bromo, or iodo), where $R^5$ and $R^6$ are independently hydrogen, lower alkyl or lower alkenyl; and $R^4$, $R^{4'}$ and $R^{4''}$ are independently branched or unbranched $C_1$ to $C_6$ alkyl, hydroxyalkyl or alkoxyalkyl. Examples of such molecules may be found in International Patent application WO98/52951, and WO97/31921, herein incorporated by reference.

Compounds of particular interest include triptolide, tripdiolide, triptonide, tripterinin, 16-hydroxytriptolide, triptriolide, and tripchloride; as well as derivatives of triptolide, 16-hydroxytriptolide and tripdiolide (2-hydroxytriptolide) that are derivatized at one or more hydroxyl groups. Such derivatives may be ester derivatives, where the attached ester substituents include one or more amino or carboxylate groups. Prodrugs of particular interest include triptolide succinate sodium salt and triptolide succinate tris(hydroxymethyl)aminomethane salt.

The compounds of the invention may be prepared from triptolide, tripdiolide, or 16-hydroxytriptolide obtained from the root xylem of the Chinese medicinal plant *Tripterygium wilfordii* or from other known sources. Methods for preparing triptolide and related compounds are known in the art.

Anti-proliferative agents: agents that act to reduce cellular proliferation are known in the art and widely used. Such agents include alkylating agents, such as nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc. Such agents are used in the treatment of cancer, as well as being immunosuppressants and anti-inflammatory agents.

Antimetabolite agents include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc. Methotrexate is widely used as an immunosuppressant, particularly with allogeneic organ transplants, as well as in the treatment of other hyperproliferative disorders. Leucovorin is useful as an anti-infective drug.

Other natural products include azathioprine; brequinar; alkaloids and synthetic or semi-synthetic derivatives thereof, e.g. vincristine, vinblastine, vinorelbine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithrmycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Hormone modulators include adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine. Other antiproliferative agents of interest include immunosuppressants, e.g. mycophenolic acid, thalidomide, desoxyspergualin, azasporine, leflunomide, mizoribine, azaspirane (SKF 105685), etc., taxols, e.g. paclitaxel, etc.

Retinoids, e.g. vitamin A, 13-cis-retinoic acid, trans-retinoic acid, isotretinoin, etc.; carotenoids, e.g. beta-carotene, vitamin D, etc. Retinoids regulate epithelial cell differentiation and proliferation, and are used in both treatment and prophylaxis of epithelial hyperproliferative disorders.

Angiotensinase inhibitors diminish exposure of the mesangium to protein factors that stimulate mesangial cell proliferation, and are useful with respect to vascular proliferative disorders.

An agent of particular interest for the present methods is irinotecan (CPT-11), a topoisomerase I inhibitor. CPT-11 finds use as a co-therapeutic agent, e.g. in the treatment of solid tumors, such as colon cancer, sarcomas, non-small cell lung carcinoma, ovarian and endometrial carcinomas, adenocarcinomas, mesotheliomas, etc. Other topoisomerase inhibitors of interest in the subject methods include doxorubicin and carboplatinum, which inhibit type II topoisomerase.

Pharmaceutical Formulations: The diterpenoid triepoxides, and the anti-proliferative agents can be incorporated into a variety of formulations for therapeutic administration. The diterpenoid triepoxide and anti-proliferative agent can be delivered simultaneously, or within a short period of time, by the same or by different routes. In one embodiment of the invention, a co-formulation is used, where the two components are combined in a single suspension. Alternatively, the two may be separately formulated.

Part of the total dose may be administered by different routes. Such administration may use any route that results in systemic absorption, by any one of several known routes, including but not limited to inhalation, i.e. pulmonary aerosol administration; intranasal; sublingually; orally; and by injection, e.g. subcutaneously, intramuscularly, etc.

More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the therapeutic agent is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with each compound in the host.

Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosage: The combined use of diterpenoid triepoxides and anti-proliferative agents has the advantages that the required dosages for the individual drugs is lower, and the effect of the different drugs complementary. Depending on the patient and condition being treated and on the administration route, the diterpenoid triepoxides will generally be administered in dosages of 0.001 mg to 5 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. The dosage for the anti-proliferative agent will vary substantially with the compound, in accordance with the nature of the agent. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Susceptible tumors: The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

Tumors of interest include carcinomas, e.g. colon, prostate, breast, melanoma, ductal, endometrial, stomach, dysplastic oral mucosa, invasive oral cancer, non-small cell lung carcinoma, transitional and squamous cell urinary carcinoma, etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

The majority of breast cancers are adenocarcinomas subtypes. Ductal carcinoma in situ is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Methods of Use

A combined therapy of diterpenoid triepoxide compounds and anti-proliferative agents is administered to a host suffering from a hyperproliferative disorder. Administration may be topical, localized or systemic, depending on the specific disease. The compounds are administered at a combined effective dosage that over a suitable period of time substantially reduces the cellular proliferation, while minimizing any side-effects. Where the targeted cells are tumor cells, the dosage will usually kill at least about 25% of the tumor cells present, more usually at least about 50% killing, and may be about 90% or greater of the tumor cells present. It is contemplated that the composition will be obtained and used under the guidance of a physician for in vivo use.

To provide the synergistic effect-of a combined therapy, the diterpenoid triepoxide active agents can be delivered together or separately, and simultaneously or at different times within the day. In one embodiment of the invention, the diterpenoid triepoxide compounds are delivered prior to administration of the anti-proliferative agents.

The susceptibility of a particular tumor cell to killing with the combined therapy may be determined by in vitro testing, as detailed in the experimental section. Typically a culture of the tumor cell is combined with a combination of a antiproliferative agents and a diterpenoid triepoxide at varying concentrations for a period of time sufficient to allow the active agents to induce cell killing. For in vitro testing, cultured cells from a biopsy sample of the tumor may be used. The viable cells left after treatment are then counted.

The dose will vary depending on the specific antiproliferative agents utilized, type of cells targeted by the treatment, patient status, etc., at a dose sufficient to substantially ablate the targeted cell population, while maintaining patient viability. In some cases therapy may be combined with stem cell replacement therapy to reconstitute the patient hematopoietic function.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the array" includes reference to one or more arrays and equivalents thereof known to those skilled in the art, and so forth. All technical and scientific terms used herein have the same meaning as commonly understood to one of ordinary skill in the art to which this invention belongs unless clearly indicated otherwise.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

EXAMPLE 1

In vivo Antitumor Activity of a Derivative of Triptolide

Materials and Methods

Cells and Transfections. H23 (non-small cell lung cancer) and ZR-75 (breast cancer) cell lines were purchased from ATCC. The Bcl-2 expression vector was provided by Fred Hutchinson Cancer Research Center, Seattle, Wash. MES-SA and Dx5 cell lines were provided by Branimir Sikic (Stanford University). Cells were cultured in the appropriate medium with 10% FCS supplemented with L-glutamine, penicillin and streptomycin. To examine the effect of Bcl-2 on cell survival, the Bcl-2 expression vector or the vector alone was co-transfected with a β galactosidase expression vector (Invitrogen, Carlsbad, Calif.) at a 5:1 ratio using lipofectamine plus (GIBCO BRL, Gaithersburg, Md.) into Dx5 cells. After 36 h cells were stained with 5-bromo-4-chloro-3-indolyl □-D-galactopyranoside (X-gal). Cell survival was calculated as number of total cells-blue cells/total number of cells in a 90 mm² area from duplicate plates and expressed as the mean±S.D.

Cell death reagents and assays. Cell viability was measured by an MTT assay as recently described (Lee et al. (1999) *J. Biol. Chem.* 274:13451–13455. z-VAD-fluoromethylketone (z-VAD.fmk) was obtained from Alexis Biochemicals, San Diego, Calif. The effect of z-VAD.fmk on cell viability was analyzed by annexin and propidium iodide staining followed by FACS analysis according to the manufacturer's protocol (Clontech Laboratories, Palo Alto, Calif.). The analysis of apoptosis in histologic sections was done by terminal deoxynucleotidyl transferase (TdT)-mediated d-UTP nick end labeling (TUNEL) of slides from paraffin sections of day 3 tumors harvested from the mice 24 h after the second of two daily treatments with PG490-88 or saline. TUNEL staining was done according to the manufacturer's protocol (Boehringer Mannheim, Indianapolis, Ind.) and then the histology slides were counterstained with methyl green. DNA was isolated from cells for analysis of internucleosomal DNA laddering followed by agarose gel electrophoresis and ethidium bromide staining.

Purification of PG490 and PG490-88. PG490 (triptolide) is composed of white to off-white crystals, has a melting point of 226–240° C., produces a single spot on thin layer chromatography, conforms to a standard triptolide preparation by Proton Nuclear Magnetic Resonance, is 97% pure by reverse phase HPLC evaluation using acetonitrile:water:methanol, and is within 0.4% of the theoretical result for elemental analysis (66.51% C, 6.43% H compared to the theoretical values of 66.65% C, 6.71% H).

PG490-88, 14-succinyl triptolide sodium salt prepared semisynthetically from PG490, is composed of white amorphous powder, has a melting point of 232–250° C., produces a single spot on thin layer chromatography, conforms to a standard PG490-88 preparation by Proton Nuclear Magnetic Resonance, and is 98% pure by reverse phase HPLC evaluation using acetonitrile:methanol: 0.006M sodium phosphate pH=3.2. PG490-88 is a prodrug of PG490, with a half-life in mouse serum of <5 min at room temperature. Stock solutions of PG490-88 (1 mg/ml) were prepared by dissolution in 0.9% NaCl and sterilized by microfiltration using 0.2 μm pore size filters (Supor Acrodisc 25, Gelman Sciences, Ann Arbor, Mich.). The PG490-88 stock solutions were diluted in 0.9% NaCl for IP administration.

Doxorubicin (Gensia Laboratories, Ltd., Irvine, Calif.) purchased as a stock solution of 200 mg/ml was prepared for IP administration by dilution in 0.9% NaCl. Taxol was prepared by dissolution in ethanol and addition of an equal volume of cremophor EL (Sigma, St. Louis, Mo.) to produce a stock solution of 30 mg/ml, which was diluted in 0.9% NaCl for IP administration.

Nude mouse xenograft model. Female NCr nude mice were purchased from Taconic, Germantown, N.Y., and were generally 20–24 grams when used. Mice were kept in autoclaved filter-top microisolator cages with autoclaved water and sterile food ad lib. The cages were maintained in an isolator unit providing filtered air (Lab Products, Inc., Maywood, N.J.). Tumor cells were grown and harvested as described above. NCr nude mice were injected intradermally with $5\times10^6$ tumor cells. In some experiments, treatment was initiated on the day of tumor cell implantation. Otherwise, tumor size was monitored, the mice were grouped together to constitute a similar mean tumor size in each group in an experiment, and treatment was initiated. Mice were treated IP daily for 5 days per week.

Results

PG490 (triptolide) induces apoptosis in tumor cells in vitro. PG490 alone was found to be cytotoxic on tumor cell lines which include H23 cells, a non-small cell lung cancer cell line with mutant p53, Dx5 cells, an MDR uterine sarcoma cell line derived from the MES-SA parent cell line and ZR-75 cells, a breast cancer cell line. Dx5 cells are 100-fold more resistant to doxorubicin and 1000-fold more resistant to taxol than the MES-SA parent cell line (Chen et al. (1994) *Cancer Res.* 54:4980–4987). PG490 at a dosage of 10 ng/ml decreased cell viability by 65–70% of cells in the H23 and Dx5 cell lines and by 24% of cells in the ZR-75 cell line. PG490 at 20 ng/ml reduced cell viability by greater than 80% in all three cell lines (FIG. 1).

In FIG. 1A, ZR-75 (breast cancer), H23 (non-small cell lung cancer) and Dx5 (MDR uterine sarcoma) cell lines were treated with PG490 at dosages shown and harvested 48 h later for analysis of cell viability by an MTT assay. Data is the mean of three experiments±S.D. In FIG. 1B, DNA was isolated from untreated or PG490-treated cells 16 h after the addition of PG490 followed by agarose gel electrophoresis and ethidium bromide staining.

No significant difference in sensitivity to PG490 was observed between the Dx5 cell line and its parent MES-SA cell line. To confirm that PG490-induced cell death was apoptotic, the presence of PG490 induced DNA laddering in Dx5 cells was examined, and it was found that PG490 induced DNA laddering in Dx5 cells which began at 6 h and was maximal by 16 h.

Figure 2:
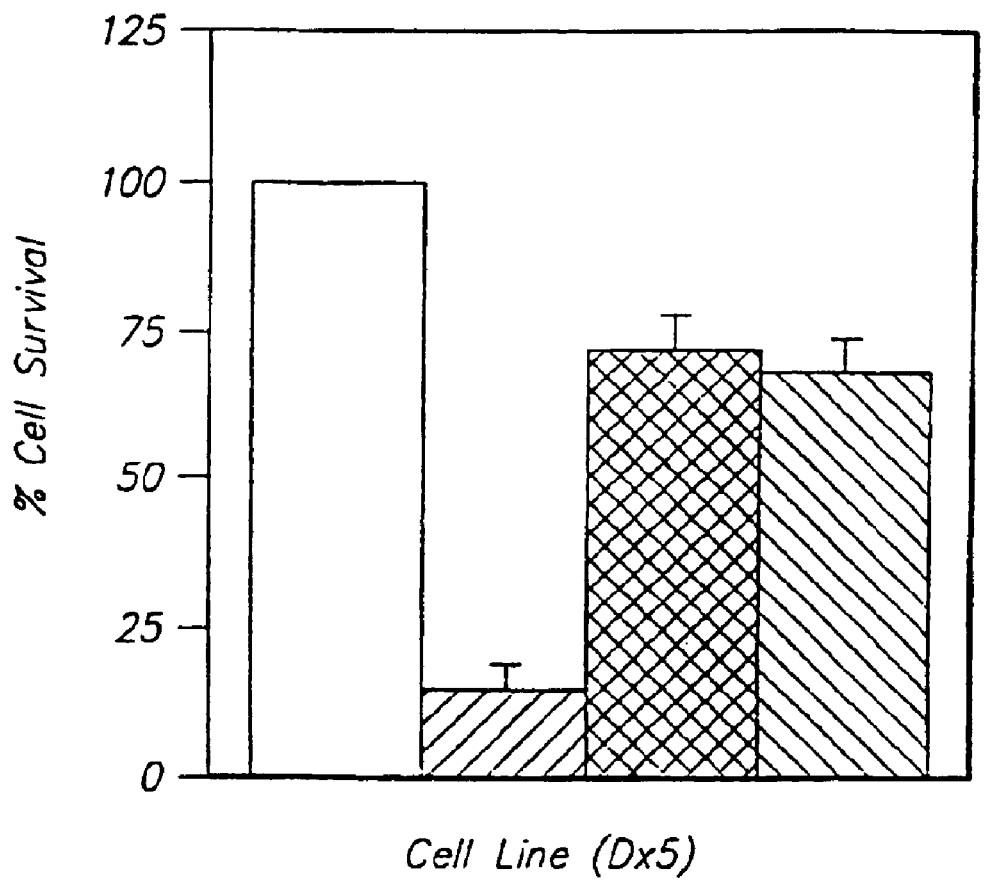
FIG. 2 is a graph depicting the inhibition of PG490-induced apoptosis.

PG490 (triptolide) did not cause growth arrest or significantly affect cell cycle progression in Dx5 and H23 cells. Overexpression of Bcl-2 was observed to increase the cell survival in PG490-treated Dx5 cells from 15% to 72% (FIG. 2). z-VAD.fmk,(100 □M), a tetrapeptide caspase inhibitor, also increased cell viability in PG490-treated Dx5 cells from 15% to 68% (FIG. 2). Bcl-2 or vector control was transiently transfected into Dx5 cells followed by the addition of PG490 (20 ng/ml) and stained 36 h later with X-gal. % cell survival was calculated as total cells-blue cells/total cells×100. z-VAD.fmk (100 □M) was added to Dx5 cells 1 h prior to the addition of PG490 (20 ng/ml) and cells were harvested for analysis of cell viability 36 h later by annexin and propidium iodide staining followed by FACS analysis. Data represents the mean of three replicates from two independent experiments±S.D.

PG490-88 prevents human tumor development in nude mice. The results reported above show cytotoxicity of PG490 on tumor cells in vitro. To extend these studies to an in vivo setting using human tumor cell xenografts, PG490-88 was used, a more easily administered, water soluble prodrug of PG490. H23 tumor cells were implanted intradermally in nude mice and the animals were left untreated or were injected IP daily with PG490-88 starting at the time of implantation. Tumors arose in 5/5 of the untreated mice but no tumors were observed after 5 or 7 weeks of dosing with PG490-88 at doses ranging from 0.25 to 0.75 mg/kg/day (Table 1). PG490-88 treatment was stopped after week 5 in 3 mice per group and was continued for an additional 2 weeks in 2 mice per group. A visible tumor arose during the sixth week in one animal in each group in which PG490-88 dosed at 0.5 mg/kg/day or less was stopped but no more visible tumors appeared in these groups after week 6 (Table 1). No visible tumors developed in any of the mice through the 10 weeks of observation in mice which received 0.75 mg/kg/day of PG490-88.

TABLE 1

PG490-88 Treatment of Nude Mice Prevents Formation of Human Tumor Xenografts

| | Number of mice in group with a tumor | | |
|---|---|---|---|
| | WEEK 5 | Week 6 | Week 10 |
| Untreated | 5/5 | 5/5 | 5/5 |
| PG490-88 (mg/kg/day) | | | |
| 0.25 | 0/5 | 1/5 | 1/5 |
| 0.375 | 0/5 | 1/5 | 1/5 |
| 0.5 | 0/5 | 1/5 | 1/5 |
| 0.75 | 0/5 | 0/5 | 0/5 |

Nude mice were implanted with H23 tumor cells (day 0). Mice were left untreated, or were injected IP with PG490-88 daily from the day of tumor cell implantation for 5 consecutive days per week. PG490-88 was administered for 5 weeks. The untreated group consisted of 5 mice. Three mice in each of the treatment groups received PG490-88 for 5 weeks, and 2 mice in each of these groups were given PG490-88 for 2 additional weeks (7 weeks total). The tumor appeared only in mice in which treatment had been stopped after 5 weeks.

Figure 3:
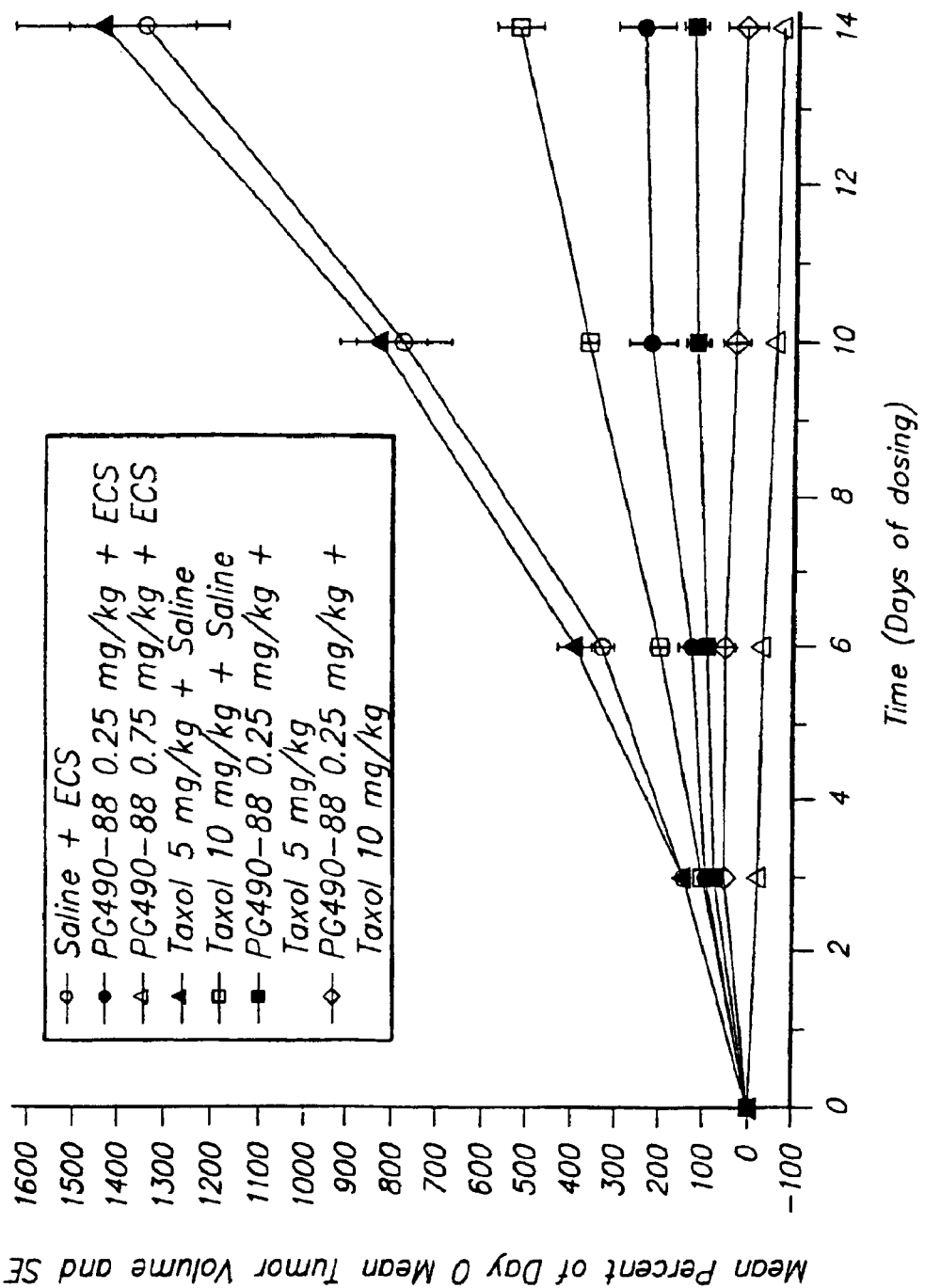
FIG. 3 illustrates the effect of PG490-88 on preestablished H23 tumors.

PG490-88 inhibits the growth of established tumors of H23 human tumor cells and displays enhanced efficacy in combination therapy with taxol. H23 tumor cells were implanted intradermally in nude mice. When the tumors reached approximately 100 mm$^3$, daily IP treatment with PG490-88 was initiated. PG490-88 inhibited tumor growth in a dose-dependent manner (FIG. 3). The data in FIG. 3 represents the measurement of H23 tumor volume on day 14 after the initiation of treatment. Nude mice bearing xenografts of H23 human tumor cells were treated daily as shown. The data represent the means and the standard errors of the means of the tumor volumes as percent of the day 0 tumor volumes for each animal measured day 3, 6, 10 and 14 days after the initiation of treatment. There were 5 mice per group.

By day 14, the 0.25 mg/kg/day dose of PG490-88 reduced tumor volume to 21% of the volume of the vehicle control. PG490-88 at 0.75 mg/kg/day progressively reduced the mean tumor volume from day 3 through day 14, decreasing the mean tumor size by 61% from the initial value at day 0 and a decrease of 97% relative to the day 14 vehicle control (FIG. 3). Taxol decreased tumor growth at the higher dose (10 mg/kg/day) but not the lower dose (5 mg/kg/day), with a day 14 mean tumor volume 42% of the vehicle control (FIG. 3). PG490-88 at 0.25 mg/kg/day plus 10 mg/kg/day of taxol decreased tumor size by 93% relative to the day 14 vehicle control volume (FIG. 3). Taxol at 15 mg/kg/day was not used because of toxicity.

A histologic section of an H23 tumor three days after treatment with PG490-88 showed many cells with abundant eosinophilic cytoplasm, pyknotic nuclei with thinning or loss of nuclear membrane and condensed chromatin compared to a pattern of more homogenous spindle-shaped cells with an increased nuclear:cytoplasmic ratio in the saline-treated control. Also, many TUNEL-positive cells were seen in the PG490-88-treated group in comparison to saline-treated animals. At day 15 after the initiation of treatment with PG490-88, the H23 tumor was replaced by fibrous scar tissue with a central area of calcium phosphate precipitation but the saline-treated control was unchanged in appearance compared to the day 3 saline-treated control.

PG490-88 inhibits the growth of established tumors of an MDR human tumor cell line. MDR is a factor in failing to achieve durable chemotherapeutic efficacy in the clinical setting. Using an MDR tumor cell line Dx5 the efficacy of PG490-88 was tested. Nude mice were implanted intradermally with Dx5 tumor cells, and treatment was initiated when the tumors reached approximately 100 mm$^3$. The mean tumor volume increased more than 10-fold over the 14 days from the beginning of treatment in the groups of mice receiving saline or doxorubicin alone at 2 mg/kg/day (FIG. 4).

Figure 4:
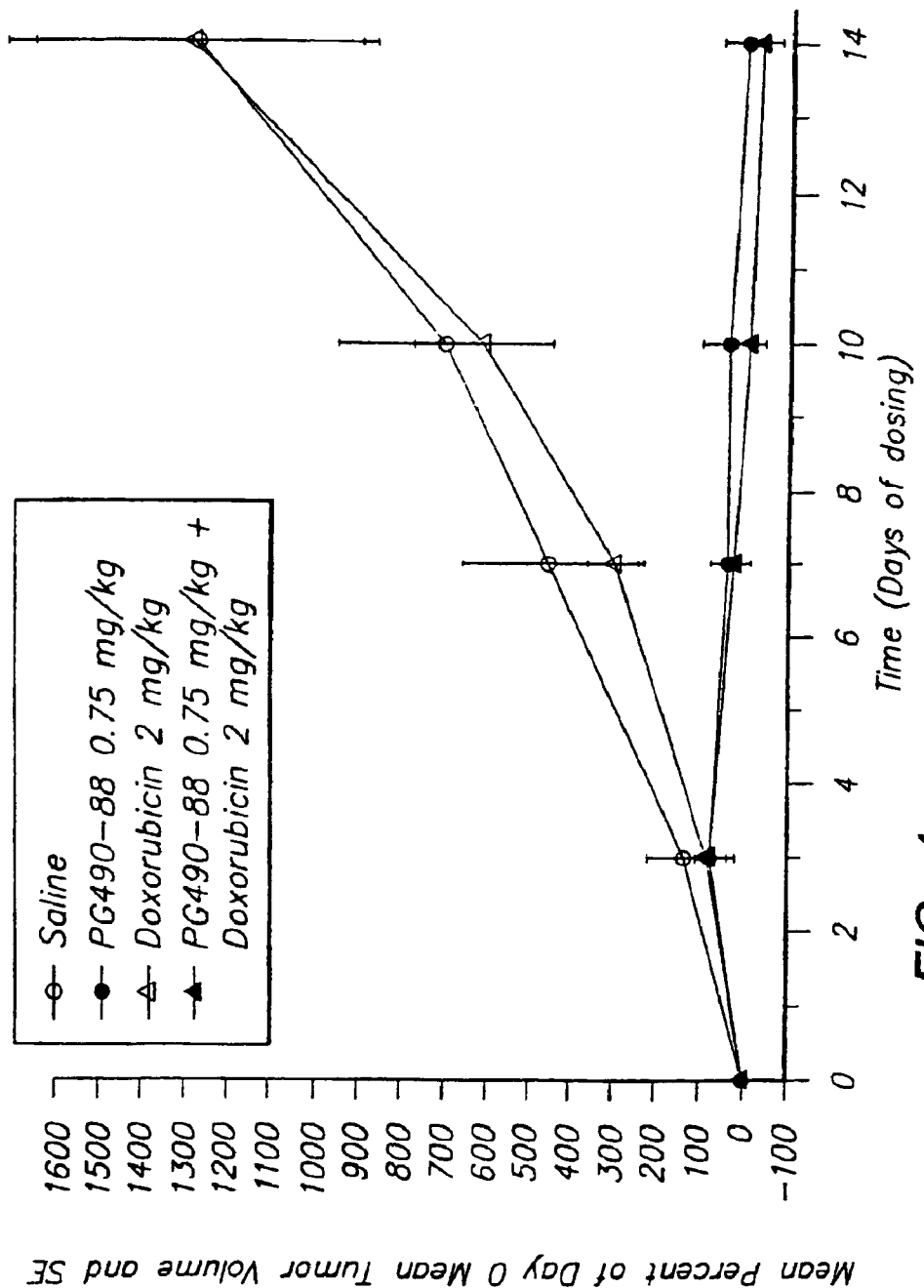
FIG. 4 depicts the effect of PG490-88 on preestablished Dx5 MDR tumors.

The data in FIG. 4 represents the measurement of Dx5 tumor volume on day 14 after the initiation of treatment. Nude mice bearing xenografts of Dx5 MDR human tumor cells were treated daily as shown. The data represent the means and the standard errors of the means of the tumor volumes as percent of the day 0 tumor volumes for each animal measured day 3, 7, 10 and 14 days after the initiation of treatment. There were 5 mice in the groups receiving saline or PG490-88 plus doxorubicin, and 4 mice in the groups receiving PG490-88 or doxorubicin alone.

PG490-88 at 0.75 mg/kg/day reduced the mean tumor size by 28% in three of the four mice compared to the day 0 values. One tumor grew by 2.8-fold compared with its day 0 value. By day 14, combination treatment with PG490-88 and doxorubicin produced a 34% reduction in tumor volume from day 0 and a 94% reduction in mean tumor volume relative to the day 14 vehicle control volume, with all of the tumors decreasing in size compared to the day 0 values.

The in vivo studies described above used PG490-88, a succinate salt prodrug of triptolide which is rapidly converted to triptolide in the serum. The dosage of triptolide, based on a molar comparison to PG490-88, was 70 μg/mouse/week and it was well tolerated. It was observed that PG490-88 at a dosage of 0.75 mg/kg completely prevented H23 tumor formation in all mice and tumors did not emerge in any of the mice 5 weeks after dosing with PG490-88 was stopped.

PG490-88 also markedly inhibited the growth of preestablished H23 tumors and induced apoptotic cell death in the tumor cells. Additionally, the combination of PG490-88 (0.25 mg/kg) plus taxol (10 mg/kg) was more tumoricidal than either agent alone in preventing tumor formation by H23 cells. In preestablished tumors derived from the MDR Dx5 cell line PG490 markedly inhibited tumor growth and doxorubicin did not interfere with the tumoricidal activity of PG490-88. There was no observable toxicity in mice treated with PG490-88 (0.75 mg/kg) as measured by a change in body weight, altered activity or labored respiration.

There has been progress in the treatment of some solid tumors but significant increases in long term survival have been limited by the development of p53 mutant and multi-drug resistant tumors and by the toxicity of chemotherapy. The above results demonstrate that PG490-88 alone is a safe and potent tumoricidal agent in vivo against a p53 mutant and an MDR tumor, and that the tumoricidal activity of PG490-88 is enhanced by treatment with chemotherapeutic agents such as taxol.

EXAMPLE 2

Triptolide Induces Apoptosis in Solid Tumor Cells and Enhances Chemotherapy-induced Apoptosis p53 plays a role in triptolide-induced apoptosis in tumor cell lines. Also, triptolide enhances apoptosis induced by DNA-damaging chemotherapeutic agents through the p53 pathway. However, the triptolide-mediated increase in p53 results in repression of mdm2 and p21$^{Cip1/Waf1}$ transcription. In addition, the levels of the Mdm2 and p21 protein in triptolide-treated cells decrease late after the addition of triptolide. Interestingly, triptolide induces translation of p53 without initially affecting p53 protein stability. These findings demonstrate that triptolide-induced apoptosis and its enhancement of chemotherapy-induced apoptosis in p53 wild-type cells are mediated, at least in part, by the induction of p53 translation.

Material and Methods

Reagents. PG490 (triptolide, MW 360) was obtained from Pharmagenesis (Palo Alto, Calif.). A549 (non-small cell lung cancer) and HT1080 (fibrosarcoma) cell lines were from ATCC. MCF-7 (breast cancer) cell line was obtained from Dr. Ron Weigel (Stanford University). Mouse embryonic fibroblasts (p53+/+ and p53−/−) cell lines were provided by Dr. Amato J. Giaccia (Stanford University). Doxorubicin, cycloheximide, and 3-(4,5-dimethylthiazol-2-yl)-2,5-diphenyltetrazolium bromide (MTT) were obtained from Sigma Chemicals. The mdm2 promoter-luciferase construct pBP100-GL2 was provided by Dr. Louis Noumovski (Stanford University) and was made by cloning the Bgl II-Hind III fragment from the pBP100CAT vector into the pGL2-Basic Vector (Promega, Madison, Wis.). MCF-7 cells were transfected using lipofectamine Plus reagent from the Life Technologies, Inc. Cells were collected and lysates were prepared according to the manufacturer's protocol for luciferase assay (Promega Corp., Madison, Wis.). Antibodies for p53, p21$^{WAF1/CIP1}$, Mdm2, Protein phosphatase-1 (PP-1), and Erk-2 were from Calbiochem, Inc (La Jolla, Calif.) and the rabbit polyclonal Bax antibody was from Upstate Biotechnology (Lake Placid, N.Y.).

Cell culture and luciferase assay. A549 (non-small cell lung cancer), HT-1080 (fibrosarcoma), and MCF-7 (breast cancer) cells were cultured in the appropriate media with 10% FCS supplemented with L-glutamine, penicillin, and streptomycin. p53 wild-type (+/+) and null (−/−) Mouse Embryonic Fibroblasts (MEFS) transfected with the E1A/Ras were grown in DMEM containing 15% FCS supplemented with L-glutamine, penicillin, and streptomycin. Transfections were done on MCF-7 cells using the lipofectamine Plus reagent. At 24 hours after transfection, MCF-7 cells were left untreated or treated with triptolide (20 ng/ml) or doxorubicin (100 nM) for 4, 8, and 16 hours and cells were collected for luciferase assay. Luciferase activity was measured in samples with equal protein concentration with a Luminometer (Analytical Luminescence Laboratory, San Diego, Calif.).

Cell viability assay. Cell viability was measured by an 3-(4,5-dimethylthiazol-2-yl)-2,5-diphenyltetrazolium bromide (MTT) assay as described above. Untreated or cells treated with triptolide and/or doxorubicin were harvested at the indicated times followed by the addition of MTT to the cells in a 96-well plate. Cells were solubilized with CH$_3$Cl acidified with 0.1N HCl. The 96-plate was read at a wavelength of 590 nm on an iEMS Labsystems plate reader.

RT-PCR. RNA was prepared from MCF-7 cells using Rneasy Mini Kit from Qiagen Inc. (Valencia, Calif.). cDNAs were prepared using M-MLV reverse transcriptase (Gibco) with 2 μg of total RNA. 1/20 of total cDNA was used in limited (25 cycles) PCR reactions using Taq polymerase (Gibco). The following primer pairs were used: p53 [SEQ ID NO:1] 5'-AGTCAGATCCTAGCGTCGAG-3' and 5'-[SEQ ID. NO:2] TCTTCTTTGGCTGGGGAGAG-3', mdm2, [SEQ ID NO:3] 5'-GTCAATCAGCAGGAATCATCGG-3' and [SEQ ID NO:4] 5'-CAATCAGGCATCAAAGCCCTC-3', p21, [SEQ ID NO:5] 5'-AGTGGGGCATCATCAAAAAC-3' and [SEQ ID NO:6] 5'-GACTCCTTGTTCCGCTGCTTC-3', and glyceraldehyde-3-phosphate dehydrogenase (GAPDH)-[SEQ ID NO:7] 5'-CCCATCACCATCTTCCAG-3' and [SEQ ID NO:8] 5'-ATGACCTTGCCCACAGCC-3'.

Immunoblotting. At 8 hours after triptolide and/or doxorubicin treatment cells were harvested at the times indicated and lysed using HNET buffer (50 mM HEPES pH 7.5, 100 mM NaCl, 1 mM EGTA, and 1% Triton X-100) supplemented with 1 mM DTT, 1 mM PMSF and protease inhibitors cocktail (Boehringer Mannheim, Germany). 35 μg of protein was loaded on 10% SDS-PAGE followed by transferring to PVDF membrane. Immunoblotting was performed as previously described using a p53 mouse monoclonal antibody from Oncogene Research Products (Lee et al. (1999) *J Biol Chem* 274:13451–5).

To measure p53 half-life cycloheximide (30 μg/ml) was added to MCF-7 cells 30 min after the addition of triptolide and harvested at the times shown for immunoblot analysis of p53. Immunoblot analysis using other antibodies was performed as described above. The band intensity was measured by NIH Image 1.62.

Sub-cellular fractionation of MCF-7 cells. After treatment with triptolide (5 or 20 ng/ml) and/or doxorubicin (100 nM) cytosolic and nuclear extracts were prepared as previously described (Lee et al. (1988) *Gene Anal Tech* 5:22–31) and 50 μg of each extract was used in SDS/PAGE immunoblot analysis of p53.

Metabolic labeling of MCF-7cells Cells were grown to 80% confluence followed by pretreatment with triptolide (20 ng/ml) for 6 h in the appropriate medium. Cells were washed twice with short-term labeling medium (RPMI with 5% dialyzed FCS supplemented with L-glutamine, penicillin, and streptomycin). To deplete intracellular pools of methionine short-term labeling medium was added for 15 min at 37° C., then replaced by short-term labeling medium containing 0.1 mCi/ml [$^{35}$S] methionine (Amersham, Inc.). Cells were labeled for 30 min at 37° C. and washed with ice-cold PBS before harvesting for immunoprecipitation. The cells were lysed using RIPA buffer supplemented with protease inhibitors and immunoprecipitated using an agarose-conjugated p53 mAb (Ab-6, Oncogene Research Products) followed by 10% SDS-PAGE. The intensity of labeled p53 protein was measured by NIH Image 1.62.

Results

Triptolide induces apoptosis in solid tumor cell lines and enhances chemotherapy-induced apoptosis. To determine if tumor cell lines are sensitized to chemotherapeutic agents in the presence of triptolide, a topoisomerase II inhibitor, doxorubicin, was used. Doxorubicin (100 nM alone in A549 and HT1080 cells caused only a slight decrease in cell viability, 14.3 and 6.4% respectively, after 48 hours of drug treatment (Table 1). However, in HT-1080 cells, the combination of triptolide at 5 ng/ml (2.8 nM) plus doxorubicin reduced cell viability by 65%, but triptolide at 5 ng/ml or doxorubicin (100 nM) alone reduced cell viability only by 10% and 6% respectively. Triptolide at 20 ng/ml (11.2 nM) alone reduced cell viability by 74% in HT1080 cells. Also, in A549 cells, the combination of triptolide at 20 ng/ml plus doxorubicin (100 nM) decreased cell viability by 67% but triptolide and doxorubicin alone decreased viability only by 35% and 15% respectively.

Additionally, we observed that triptolide enhances cell death in A549 cells induced by carboplatinum, another topoisomerase II inhibitor. We also examined the effect of triptolide (20 ng/ml) alone on the MCF-7 breast cancer cell line which contains wild-type p53. We found that triptolide, 5 ng/ml and 20 ng/ml, decreased cell viability by 36% and 70% respectively in MCF-7 cells (Table 2). We have also found that triptolide alone induces cell death in greater than 80% of cells in other solid tumor cell lines. Thus, triptolide alone is cytotoxic in tumor cells and it cooperates with doxorubicin to enhance cell death in tumor cell lines.

TABLE 2

Cell viability assay of human tumor cell lines after triptolide treatment

| Treatment | Percent survival[a] | | |
|---|---|---|---|
| | MCF-7 | A549 | HT-1080 |
| Triptolide 5 ng/ml | 63.9 ± 8.1 | 91.1 ± 3.8 | 90.4 ± 6.2 |
| Triptolide 20 ng/ml | 30.5 ± 7.6 | 64.0 ± 8.2 | 26.0 ± 5.2 |
| Doxorubicin 100 nM | ND[b] | 85.7 ± 9.6 | 93.6 ± 4.3 |
| Triptolide 5 ng/ml + Doxorubicin 100 nM | ND | 76.5 ± 9.9 | 35.8 ± 6.7 |
| Triptolide 20 ng/ml + Doxorubicin 100 nM | ND | 33.6 ± 11.4 | 15.5 ± 1.4 |

[a]Cell viability was measured by MTT assay after 48 h as described in Materials and Methods.
[b]Not determined.

Triptolide increases expression of p53. p53 mediates cell death responses to cytotoxic stimuli such as hypoxia, irradiation and DNA damaging chemotherapeutic agents. Since triptolide alone is cytotoxic and it cooperates with doxorubicin, it was hypothesized that triptolide-induced apoptosis may be mediated by p53. In both MCF-7 and A549 cells, which retain wild-type p53, triptolide increased p53 steady state protein levels 2–4 fold in a dose- and time-dependent manner. In MCF-7 cells doxorubicin induced a 2 fold increase in p53, and triptolide induced a greater than 4-fold increase in p53 protein. In A549 cells, the combination of triptolide (20 ng/ml) plus doxorubicin (100 nM) at 24 h showed the greatest increase (greater than a 12-fold increase) in p53. Triptolide (5 ng/ml) in combination with doxorubicin also markedly increased p53 in HT1080 cells. We next examined if the increase in the p53 protein level was due to an increase in the p53 mRNA. The levels of the p53 mRNA did not increase in response to triptolide but, in fact, p53 mRNA was slightly reduced in MCF-7 cells treated for 16 h with triptolide (FIG. 5A).

Figure 5:
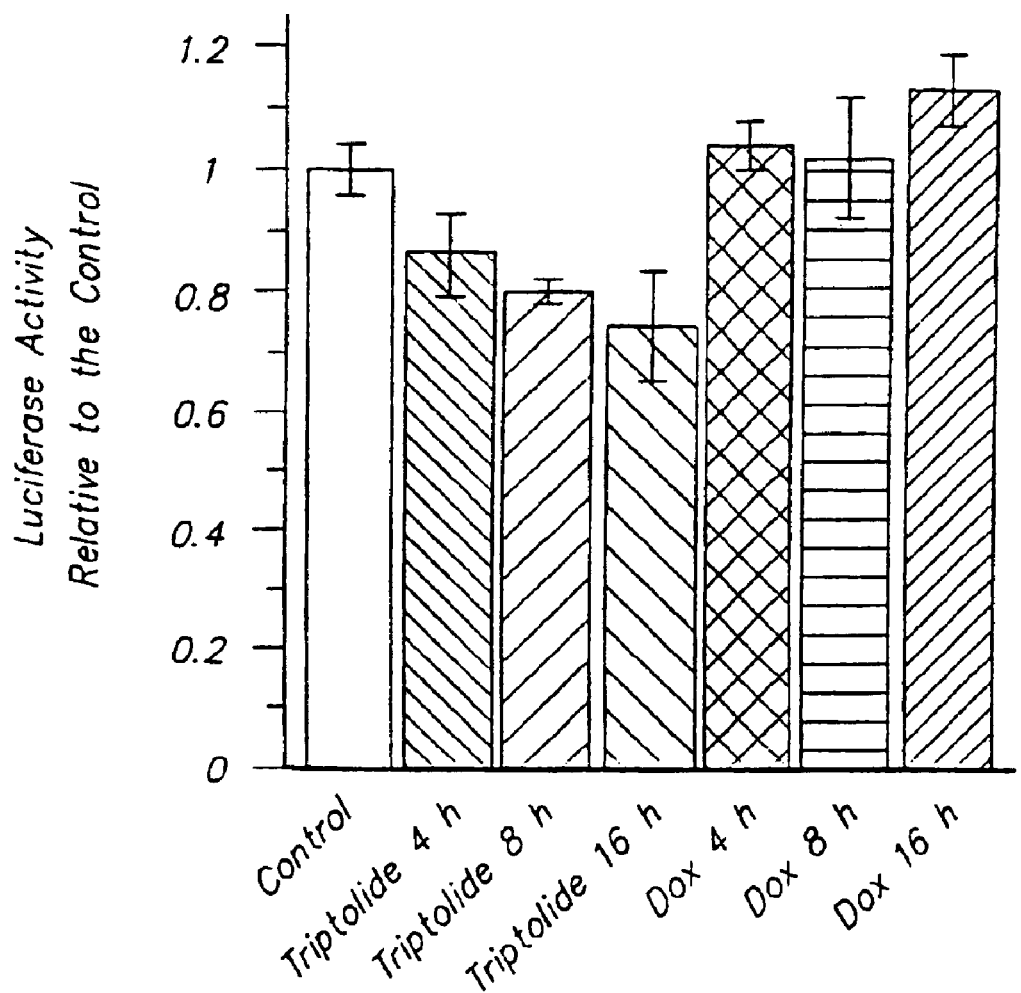
FIG. 5. Triptolide inhibits Mdm2 gene expression.

In the experiments shown in FIG. 5, RT-PCR was performed using 2 µg of total RNAs extracted from MCF-7 cells. Cells were treated with triptolide (20 ng/ml) or doxorubicin (100 nM) and harvested after 8 and 16 hours. GADPH was used as a loading control. The plasmid pBP100-GL2 which contains a p53-binding site in the mdm2 promoter was transiently transfected into MCF-7 cells, and cellular lysates were used for the luciferase assay. The values are an average of three experiments±S.D. Taken together, these data suggest that the increase in p53 is post-transcriptional in cells undergoing triptolide-induced cell death.

Functional p53 enhances triptolide-induced cell death. The outcome of many chemotherapeutic drugs or radiation therapy depends on the functional status of the tumor suppressor p53 gene. To determine if the presence of functional p53 contributes to triptolide-induced cell death, we used mouse embryonic fibroblasts (MEFs) cells with the wild-type (+/+) or null (−/−) p53 gene. Triptolide at dosages of 5 ng/ml or 10 ng/ml reduced p53+/+ MEF cell viability by 48% and 73% respectively and by 15% and 50% in p53 (−/−) cells (Table 3). In MEF cells with the wild-type p53, doxorubicin induced 35% more cell death than those without functional p53. Also, the combination of triptolide plus doxorubicin reduced cell viability by 88% in p53 (+/+) cells but only by 55% in p53 (−/−) cells. Therefore, functional p53 plays a role in mediating triptolide-induced cell death.

Expression of Mdm2 and p21 are down-regulated in cells treated with triptolide. One model of p53-mediated apoptosis is that upon cellular stresses (such as DNA damage), p53 is stabilized and this increases expression of genes such as mdm2, bax, p21$^{CiP1/Waf1}$, and gadd45. Mdm2 negatively regulates p53 stability by mediating nuclear export via direct protein binding and/or ubiquitin/proteosome degradation. In DNA damage (such as γ-irradiation), phosphorylations of p53 on serines 15 and 392 by DNA-PK or ATM interferes with the ability of Mdm2 to bind to p53 and target p53 for degradation. This results in stabilization and activation of p53.

To determine if a similar mechanism exists in triptolide-induced apoptosis, the levels of several genes that are downstream of p53 transactivation were examined. When MCF-7 cells were treated with doxorubicin 100 nM, there was about a 1.5–2 fold increase in the Mdm2 mRNA and protein. This increase in Mdm2 paralleled the increase in p53 level which also resulted in increases in bax and p21 mRNA.

In cells treated with triptolide, however, there was a time-dependent decrease in mdm2 mRNA. To measure the effect of triptolide on mdm2 gene expression, a luciferase vector was used, which contains a consensus p53-binding site from the mdm2 promoter. Despite the high levels of p53 in triptolide-treated MCF-7 cells, transactivation of the reporter construct decreased by approximately 30% in the presence of triptolide. However, doxorubicin increased transactivation of the Mdm2 by 15% by 16 h. The repression of the p53 dependent genes by triptolide is not a general effect, since gadd45 and elongation factor 1-alpha (EF-1α), which are also induced by p53, were not affected. Thus, triptolide induces p53 but represses expression of some p53 dependent genes.

To determine if the absence of an increase in p53 target genes in cells treated with triptolide is due to the lack of p53 translocation, p53 translocation into the nucleus was examined after triptolide treatment. Compared with the cells treated with doxorubicin, where the majority of p53 is translocated into the nuclei, the majority of p53 in cells treated with triptolide (20 ng/ml) was also translocated into nuclei.

There was no significant change in the levels of the Mdm2 protein in MCF-7 cells treated with 5 ng/ml of triptolide for 8 or 24 hours but triptolide reduced cell viability by only 10% at this dosage. There was an approximately 1.5-fold increase in Mdm2 in MCF-7 cells treated with 20 ng/ml of triptolide at 8 h but by 24 h there was almost a complete loss of Mdm2 protein (FIG. 4). Also, there was a 3-fold decrease in the level of p21 protein in triptolide-treated MCF-7 cells but no significant change in Bax.

Triptolide induces translation of p53. To determine the mechanism by which triptolide induces p53 we examined the effect of triptolide on p53 protein stability and translation. To examine the effect on stability we examined levels of p53 in the presence of cycloheximide (30 µg/ml) in MCF-7 cells, a dose which blocks translation. When cells were pretreated with triptolide for 0.5 h prior to the addition of cycloheximide, there was a slight increase in p53 stability at 30 min but there was no difference from untreated cells at 60 min. These data suggested that the increased steady-state level of the p53 protein in response to triptolide did not result from an increase in the half-life of the p53 protein. We then examined if triptolide induces translation of p53 by in vivo [$^{35}$S]methionine metabolic labeling of MCF-7 cells. We found, interestingly, that triptolide induced a 4.9-fold increase in p53 translation (FIG. 5B). Thus, triptolide-induced p53 accumulation is mediated by an increase in p53 translation.

Triptolide induces cell death in almost 70% of MCF-7 cells and enhances chemotherapy-induced cell death in A549 and HT1080 cells. To delineate possible mechanism(s) of triptolide-mediated apoptosis, the role of the p53 tumor suppressor gene was studied. Triptolide induced p53 protein expression in several wild-type p53 tumor cell lines and wild-type p53 significantly enhanced the cytotoxicity of triptolide. Interestingly, triptolide induced cell death in over 80% of cells in a mutant p53 lung cancer cell line so that functional p53 is not required for triptolide-induced apoptosis. The data presented here suggests that triptolide alone and in combination with DNA damaging agents mediates a p53-dependent dependent apoptotic pathway in tumor cells with wild-type p53. It was observed that triptolide increased levels of p53 at a post-transcriptional level. This was mediated by a 5-fold increase in p53.

A late decrease in Mdm2 protein in triptolide-treated cells provide an additional mechanism for the increase in p53, and a possible mechanism for how triptolide sustains induction of p53 in the-presence of DNA-damaging agents. Triptolide-mediated repression of downstream p53 genes may serve to inhibit expression of survival factors such as MAP4 and the IGF1 receptor. Since triptolide shows enhanced cytotoxicity in combination with DNA damaging agents, it may also interfere with DNA repair. Triptolide, however, does not induce DNA strand breaks as revealed by a comet assay.

The above results demonstrate that triptolide induces p53 and that functional p53 enhances triptolide-induced apoptosis. It is also shown that triptolide enhances the cytotoxicity of DNA damaging agents. The cytotoxic activity of triptolide alone and its ability to cooperate with other cytotoxic agents represents a novel method to enhance cytolysis of solid tumor cells in vivo.

EXAMPLE 3

Synergistic Combination with CPT-11

In an animal model, it was shown that the combination of CPT-11 and PG490-88 provided for synergistic killing of tumor cells.

Materials and Methods

Mice. Female NCr nude mice were purchased from Taconic, Germantown, N.Y., and were generally 20–24 grams when used. Mice were kept in autoclaved filter-top microisolator cages with autoclaved water and sterile food ad lib. The cages were maintained in an isolator unit providing filtered air (Lab Products, Inc., Maywood, N.J.).

Nude mouse xenograft model. HT1080 tumor cells were grown in tissue culture flasks and harvested using EDTA and trypsin. Cells were centrifuged and the concentration of viable cells was appropriately adjusted. Female NCr nude mice were injected intradermally with 5 million HT1080 tumor cells each. Tumor size was monitored after tumor cell implantation by measuring the width, length and thickness of the tumors and using a formula to calculate the volume. When an appropriate tumor volume was achieved, the mice were grouped together to constitute a similar mean tumor size in each group in the experiment, and treatment was initiated. Control mice were left untreated. PG490-88 treated mice received IP injections of PG490-88 in phosphate buffered saline (0.75 mg/kg) on days 0–5 and 7–11. CPT-11 treated mice were given IV injections with CPT-11 in phosphate buffered saline (11 mg/kg) on days 1, 5, and 9. Combination therapy mice received both PG490-88 and CPT-11 treatments.

Figure 6:
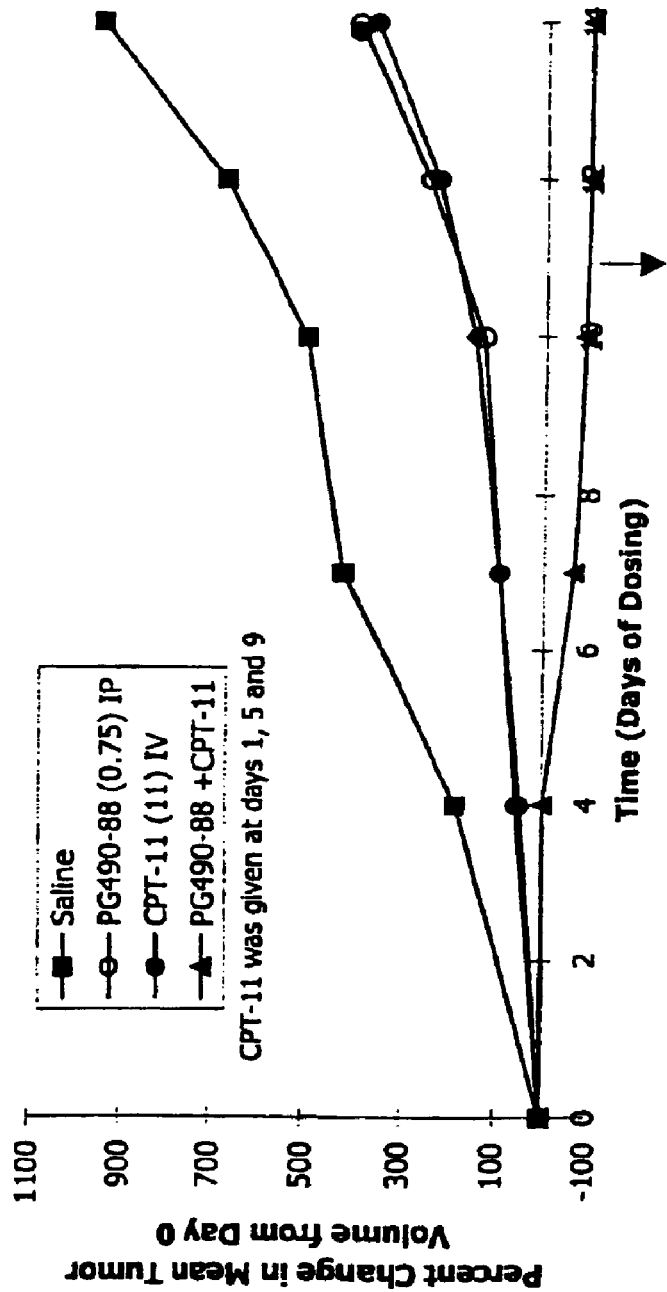
FIG. 6. PG490-88 and CPT-11 provide for a synergistic combination in treating tumors in vivo.

The results are shown in FIG. 6, and Table 3.

TABLE 3

| Summary | Day 0 | | Day 4 | | Day 7 | | Day 10 | | Day 14 | |
|---|---|---|---|---|---|---|---|---|---|---|
| | TV Mean | SE | TV Mean | SE | TV Mean | SE | TV Mean | SE | TV Mean | SE |
| Control | 103 | 15 | 293 | 49 | 536 | 69 | 616 | 164 | 980 | 380 |
| PG490-88 0.75 IP 5X/wk | 107 | 20 | 167 | 14 | 208 | 18 | 247 | 21 | 532 | 55 |
| CPT-11 11 IV every 4 days | 107 | 36 | 157 | 60 | 209 | 65 | 268 | 72 | 495 | 112 |
| PG490-88(0.75) IP + CPT-11(11) IV | 107 | 31 | 106 | 22 | 35 | 7 | 12 | 3 | 1 | 0 |

Where TV = tumor volume.

EXAMPLE 4

PG490-88 Used in Combination with Navelbine

PG490-88 exerts anticancer effects upon tumors established using the human tumor xenograft model in nude mice using cells from human tumor cell lines. Navelbine is a chemotherapeutic agent derived semisynthetically from vinbiastine that is being used more widely, partly because of a milder side effect profile. PG490-88 was tested in combination with Navelbine in nude mice bearing established HT-29 colon cancer tumors.

HT-29 tumor cells grown in tissue culture were harvested and implanted intradermally on the backs of nude mice. Tumor size was monitored by measuring the dimensions of each tumor and calculating tumor volume with a formula. When the tumors reached an appropriate size, the mice were grouped together (5 mice/group) to constitute a similar mean tumor size (approximately 100 mm$^3$), and treatment was initiated on day 0. Vehicle-treated mice received 0.9% NaCl i.p. daily for 5 days per week for 2 weeks. PG490-88 treatment at 0.25 mg/kg was administered daily i.p. 5 days per week for 2 weeks. Navelbine at 10 mg/kg was given i.v. on days 0 and 7. Mice in the combination treatment group received PG490-88 i.p. and Navelbine i.v. at the appropriate times. The treatments were given to mice at 100 µl per 10 g of mouse body weight. Tumor dimensions were measured periodically for calculation of tumor volumes.

FIG. 7 shows the change in tumor volume with treatment. The data are presented as mean percent change in tumor volume from day 0 for each treatment group. Day 0 tumor volumes are shown in Table 4. Toxicity of the treatment was monitored by weighing the mice daily 5 days per week.

In FIG. 8, a comparison is provided for tumor volumes on Days 0 and 14. Tumor dimensions were measured periodically for calculation of tumor volumes, and the final determinations were made on day 14. The data are presented as mean tumor volume in mm³ for each treatment group for the measurements on days 0 and 14.

PG490-88 at 0.25 mg/kg exerted a modest effect upon HT-29 tumor volume, with an increase by day 14 of 238% compared to the vehicle control increment of 372% from day 0, FIGS. 7 and 8, Table 4). Navelbine had little impact upon growth of HT-29 tumors, producing a 343% increase in tumor volume. Although there was little effect upon tumor growth by either agent alone, PG490-88 and Navelbine caused tumor regression when used in combination therapy. The drug combination produced a 29% reduction in mean tumor volume by day 14, and the regression was evident by day 10. As measured on day 14, the tumors on 4 of 5 of the mice in the combination therapy group had decreased in size compared to day 0.

TABLE 4

PG490-88 treatment of nude mice bearing established HT-29 human colon cancer cell line tumors.

| Treatment Group | Day 0 Tumor Volume (mm³) Mean | S.E. |
|---|---|---|
| Saline | 108 | 6 |
| PG490-88 0.25 mg/kg | 109 | 7 |
| Navelbine 10 mg/kg | 109 | 6 |
| PG490-88 0.25 mg/kg + Navelbine 10 mg/kg | 108 | 7 |

Nude mice with established HT-29 tumors were grouped together to constitute a similar mean tumor size in each group, and the mean tumor volumes and standard errors (SE) on day 0 are presented.

EXAMPLE 5

Heterotopic Heart Transplantation in the Rat Receiving PG490-88 Alone or With FK506

Materials and Methods

Animals. Inbred male rats were used. Lewis rats (RT1[1]) weighing 194 to 228 g were used as recipients. ACI rats (RT1[a]) weighing 128 to 170 g were used as heart donors.

Hearts were transplanted heterotopically in the neck by a modification of Heron's method anastomosing the donor aorta and pulmonary artery. The recipients abdomens were palpated daily, and rejection was established by cessation of heartbeat. The recipients of which the heartbeat stopped within 4 days after grafting were excluded from statistical analysis as technical failures.

Drug Administration. PG490-88 was dissolved in distilled water at 5 mL/kg and administered once a day orally (p.o.). FK506 was dissolved in saline by the volume of 1 ml/kg and administered once a day by intramuscular injection (i.m.). The drugs were given from the day of grafting (day 0) for as long as 2 weeks (day 13).

Experimental groups were as follows:
PG490-88 monotherapy groups
   0.1 mg/kg p.o. (n=7)
   0.3 mg/kg p.o. (n=8)
   1.0 mg/kg p.o. (n=8)
   Combination therapy groups
   FK506 0.032 mg/kg i.m.+Distilled water (Vehicle) p.o. (n=8)
   FK506 0.032 mg/kg i.m.+PG490-88 0.1 mg/kg p.o. (n=8)
   FK506 0.032 mg/kg i.m.+PG490-88 0.3 mg/kg p.o. (n=8)
   FK506 0.032 mg/kg i.m.+PG490-88 1.0 mg/kg p.o. (n=8)

Results

The results of PG490-88 alone, or in combination with the subtherapeutic dose (0.032 mg/kg i.m.) of FK506 in heterotopic rat heart transplantation are summarized in Table 5 and 6.

In allografting between ACI donors and Lewis recipients, the median graft survival time (MST) in the untreated, control rats was 5 days. Monotherapy with 0.1 and 0.3 mg/kg p.o. of PG490-88 was not effective, producing a MST of 6 and 5 days, respectively. However, graft survival was significantly prolonged about two times by 1 mg/kg p.o. of PG490-88 (MST; 5 to 12).

TABLE 5

Effect of PG490-88 monotherapy on survival of heart grafts from ACI donor to Lewis recipients

| PG490-88 (mg/kg p.o.) | N | Graft survival (days) | MST (days) |
|---|---|---|---|
| (untreated) | 7 | (4, 5, 5, 5, 6, 6, 8) | 5 |
| 0.1 | 7 | (4, 5, 5, 6, 6, 6, 6) | 6 |
| 0.3 | 8 | (5, 5, 5, 5, 5, 7, 7, 8) | 5 |
| 1.0 | 8 | (8, 8, 10, 12, 12, 15, 15, 16)[##] | 12 |

Drug was given from the day of allografting for as long as 2 weeks.
[##]: P < 0.01 vs untreated (Peto test)

The subtherapeutic dose of FK506 caused barely detectable increase in graft survival (MST; 5 to 8). Combined with this small dose of FK506, PG490-88 prolonged the graft survival in a dose dependent manner. It is noteworthy that 0.3 mg/kg of PG490-88, which was not effectective as monotherapy, showed some effectiveness in combination therapy. Remarkable efficacy was shown with the PG490-88 (1 mg/kg p.o.) and FK506 combination group. In this group, no rejection was observed during administration period (2 weeks) and MST was significantly prolonged (MST; 8 to 27). All doses of PG490-88 alone, or combined with FK506 were well tolerated.

TABLE 6

Effect of Combination Therapy of PG490-88 and FK506 on survival of heart grafts deom ACI donor to Lewis Recipients

| FK506 0.032 mg/kg i.m. + PG490-88 (mg/kg p.o.) | N | Graft Survival (days) | MST Days |
|---|---|---|---|
| +vehicle | 8 | 6, 8, 8, 8, 8, 9, 12, 22 | 8 |
| 0.1 | 8 | 6, 6, 9, 10, 12, 12, 12, 23 | 11 |
| 0.3 | 8 | 10, 10, 11, 12, 16, 16, 19, 19 | 14 |
| 1.0 | 7 | 24, 25, 26, 27, 28, 28, >28 | 27 |

It is evident from these data that while monotherapy of PG490-88 (1 mg/kg p.o.) prolonged the survival of heterotopic heart grafts in rats, the combination of PG490-88 and a subtherapeutic dose of FK506 0.032 mg/kg i.m.) provides for a highly synergistic and effective method of immunosuppression.

What is claimed is:

1. A method for immunosuppression in allograft transplantation, the method comprising:
   contacting a targeted immune cell population with a synergistic combination of a subtherapeutic dose of a macrocyclic immunosuppressant; and a substantially pure semi-synthetically produced triptolide ester derivative;
   in a combined dosage effective to substantially immunosuppress said targeted immune cell population.

2. The method of claim 1, wherein said macrocyclic immunosuppressant is selected from the group consisting of cyclosporin, FK506 and rapamycin.

3. The method of claim 1, wherein said macrocyclic immunosuppressant is FK506.

4. The method of claim 1, wherein said semi-synthetically produced triptolide ester and said macrocyclic immunosuppressant are administered in a co-formulation.

5. The method of claim 1, wherein said semi-synthetically produced triptolide ester and said macrocyclic immunosuppressant are separately formulated.

6. The method according to claim 1, wherein said allograft is a heart.

7. The method according to claim 1, wherein graft survival is prolonged at least about two times relative to graft survival of monotherapy with said semi-synthetically produced triptolide ester.

8. A method for immunosuppression in an inflammatory autoimmune disease, the method comprising:
   contacting a targeted immune cell population with a synergistic combination of a macrocyclic immunosuppressant; and substantially pure semi-synthetically produced triptolide ester;
   in a combined dosage effective to substantially immunosuppress said targeted immune cell population.

9. The method of claim 8, wherein said macrocyclic immunosuppressant is selected from the group consisting of cyclosporin, FK506 and rapamycin.

10. The method of claim 8, wherein said macrocyclic immunosuppressant is FK506.

11. The method according to claim 8, wherein said inflammatory autoimmune disease is arthritis.

12. The method according to claim 1 wherein said triptolide ester derivative is at least 98% pure.

13. The method according to claim 8, wherein said triptolide ester derivative is at least 98% pure.

* * * * *